United States Patent
Kaneko

(10) Patent No.: US 9,632,300 B2
(45) Date of Patent: Apr. 25, 2017

(54) IMAGE PROCESSING APPARATUS, MICROSCOPE SYSTEM, IMAGE PROCESSING METHOD, AND COMPUTER-READABLE RECORDING MEDIUM

(71) Applicant: OLYMPUS CORPORATION, Tokyo (JP)

(72) Inventor: Yoshioki Kaneko, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 381 days.

(21) Appl. No.: 14/288,674

(22) Filed: May 28, 2014

(65) Prior Publication Data

US 2014/0268320 A1  Sep. 18, 2014

Related U.S. Application Data

(63) Continuation of application No. PCT/JP2012/079710, filed on Nov. 15, 2012.

(30) Foreign Application Priority Data

Nov. 30, 2011  (JP) .................................. 2011-263131

(51) Int. Cl.
*G02B 21/00* (2006.01)
*G02B 21/06* (2006.01)
(Continued)

(52) U.S. Cl.
CPC ......... *G02B 21/06* (2013.01); *G01N 21/6458* (2013.01); *G02B 21/16* (2013.01); *G02B 21/365* (2013.01); *G01N 2021/6421* (2013.01)

(58) Field of Classification Search
CPC ..... G02B 21/06; G02B 21/16; G01N 21/6458
(Continued)

(56) References Cited

U.S. PATENT DOCUMENTS 5,371,624 A  12/1994 Nagano et al.
5,710,663 A   1/1998 Kawasaki
(Continued)

FOREIGN PATENT DOCUMENTS

JP  05-150164 A   6/1993
JP  H07-136572 A  5/1995
(Continued)

OTHER PUBLICATIONS

Japanese Office Action dated Sep. 8, 2015 from related Japanese Patent Application No. 2011-263131, together with an English language translation.
(Continued)

*Primary Examiner* — Jeffery Williams
(74) *Attorney, Agent, or Firm* — Scully, Scott, Murphy & Presser, P.C.

(57) ABSTRACT

An image processing apparatus includes an image input unit configured to input a plurality of images acquired by imaging a specimen stained with non-fluorescent dye at a plurality of wavelength bands that are different from one another and a characteristic amount calculation unit configured to calculate a characteristic amount representing autofluorescence emitted by the specimen based on the plurality of images.

12 Claims, 14 Drawing Sheets

(51) Int. Cl.
*G02B 21/16* (2006.01)
*G02B 21/36* (2006.01)
*G01N 21/64* (2006.01)

(58) Field of Classification Search
USPC .......................................................... 348/79
See application file for complete search history.

(56) References Cited

U.S. PATENT DOCUMENTS

| 2003/0144159 | A1* | 7/2003 | Akiyama | C10M 169/00 508/462 |
| 2009/0234236 | A1* | 9/2009 | Lomnes | A61B 5/026 600/504 |
| 2009/0268010 | A1* | 10/2009 | Zhao | A61B 1/00009 348/45 |
| 2010/0172555 | A1* | 7/2010 | Hasezawa | G06K 9/00127 382/128 |
| 2010/0201800 | A1 | 8/2010 | Yamamoto et al. | |

FOREIGN PATENT DOCUMENTS

| JP | H07-163572 A | 6/1995 |
| JP | 08-320437 A | 12/1996 |
| JP | 2006-153889 A | 6/2006 |
| JP | 2006-296635 A | 11/2006 |
| JP | 2008-309662 A | 12/2008 |
| JP | 2009-014939 A | 1/2009 |
| JP | 2010-181833 A | 8/2010 |
| JP | 2010-257025 A | 11/2010 |
| JP | 2010-286565 A | 12/2010 |
| JP | 2011-002341 A | 1/2011 |
| JP | 2011-179924 A | 9/2011 |
| WO | 03/010542 A1 | 2/2003 |
| WO | 2009/044846 A1 | 4/2009 |

OTHER PUBLICATIONS

Decision of a Patent Grant dated Apr. 26, 2016 in related Japanese Patent Application No. 2011-263131.
International Search Report dated Jan. 22, 2013 issued in PCT/JP2012/079710.

* cited by examiner

IMAGE PROCESSING APPARATUS, MICROSCOPE SYSTEM, IMAGE PROCESSING METHOD, AND COMPUTER-READABLE RECORDING MEDIUM

CROSS REFERENCES TO RELATED APPLICATIONS

This application is a continuation of PCT international application Ser. No. PCT/JP2012/079710 filed on Nov. 15, 2012 which designates the United States, incorporated herein by reference, and which claims the benefit of priority from Japanese Patent Application No. 2011-263131, filed on Nov. 30, 2011, incorporated herein by reference.

BACKGROUND

1. Technical Field

The present invention relates to: an image processing apparatus that performs processing of an image acquired by using a microscope; a microscope system; an image processing method; and a computer-readable recording medium.

2. Related Art

Conventionally, in observation of specimens using microscopes, various staining techniques and observation method are selected for use, according to targets to be observed or observation purposes. For example, as morphological observation staining for observing morphology of tissue and cells, non-fluorescent staining such as hematoxylin and eosin staining (hereinafter, referred to as "HE staining") using two dyes, which are hematoxylin and eosin, and Papanicolaou staining (Pap staining) are known. With respect to a specimen subjected to such morphological observation staining, bright field observation using transmitted-light illumination is usually performed in an optical microscope.

Further, for pathological observation, for example, in order to supplement morphological diagnosis based on morphology information, a molecular and pathological examination is performed in some cases, which subjects a specimen to molecule target staining for checking expression of molecular information and diagnoses functional abnormality such as abnormality in expression of a target molecule (a particular gene or protein). In this case, for example, fluorescent labeling (staining) is performed on the specimen by an immunohistochemistry (IHC) method, an immunocytochemistry (ICC) method, an in situ hybridization (ISH) method, or the like, and fluorescence observation by epi-illumination is performed, or bright field observation by performing enzyme labeling is performed.

As a technique related to observation, a method, in which the number of principal components is reduced by repeating a method combined of principal component analysis and multivariate curve resolution to remove noises in a microscope image, is disclosed in Japanese Patent Application publication No. 2010-257025, for example.

Further, in Japanese Patent Application publication No. 2010-286565, a fluorescence observation apparatus is disclosed, which graphically displays, for a plurality of images acquired based on laser light beams of wavelengths different from one another, luminance distributions, for example, as data corresponding to observation regions specified in the images.

Further, in Japanese Patent Application publication No. 2011-2341, a microscope system is disclosed, which acquires a plurality of specimen region section images acquired by imaging respective portions of a specimen region while moving, on an XY-plane, an electrically driven stage on which a specimen multiply stained by a plurality of staining dyes.

SUMMARY

In some embodiments, an image processing apparatus includes an image input unit configured to input a plurality of images acquired by imaging, at a plurality of wavelength bands that are different from one another, a specimen subjected to non-fluorescent staining, and a characteristic amount calculation unit configured to calculate, based on the plurality of images input, characteristic amount representing auto-fluorescence emitted by the specimen.

In some embodiments, a microscope system includes: the image processing apparatus; a microscope apparatus capable of fluorescence observation with respect to the specimen; and an image acquiring unit that is provided in the microscope apparatus and is configured to acquire a plurality of images by performing imaging at a plurality of wavelength bands that are different from one another.

In some embodiments, an image processing method includes the steps of: inputting a plurality of images acquired by imaging, at a plurality of wavelength bands that are different from one another, a specimen subjected to non-fluorescent staining; and calculating, based on the plurality of images input, characteristic amount representing auto-fluorescence emitted by the specimen.

In some embodiments, a non-transitory computer-readable recording medium is a recording medium with an executable program stored thereon. The program instructs a processor to perform the steps of: inputting a plurality of images acquired by imaging, at a plurality of wavelength bands that are different from one another, a specimen subjected to non-fluorescent staining; and calculating, based on the plurality of images input, characteristic amount representing auto-fluorescence emitted by the specimen.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, embodiments of an image processing apparatus, a microscope system, an image processing method, and a computer-readable recording medium according to the present invention will be described in detail with reference to the drawings. The present invention is not limited to these embodiments. Further, in describing the drawings, the same portions are appended with the same reference signs.

First Embodiment

Figure 1:
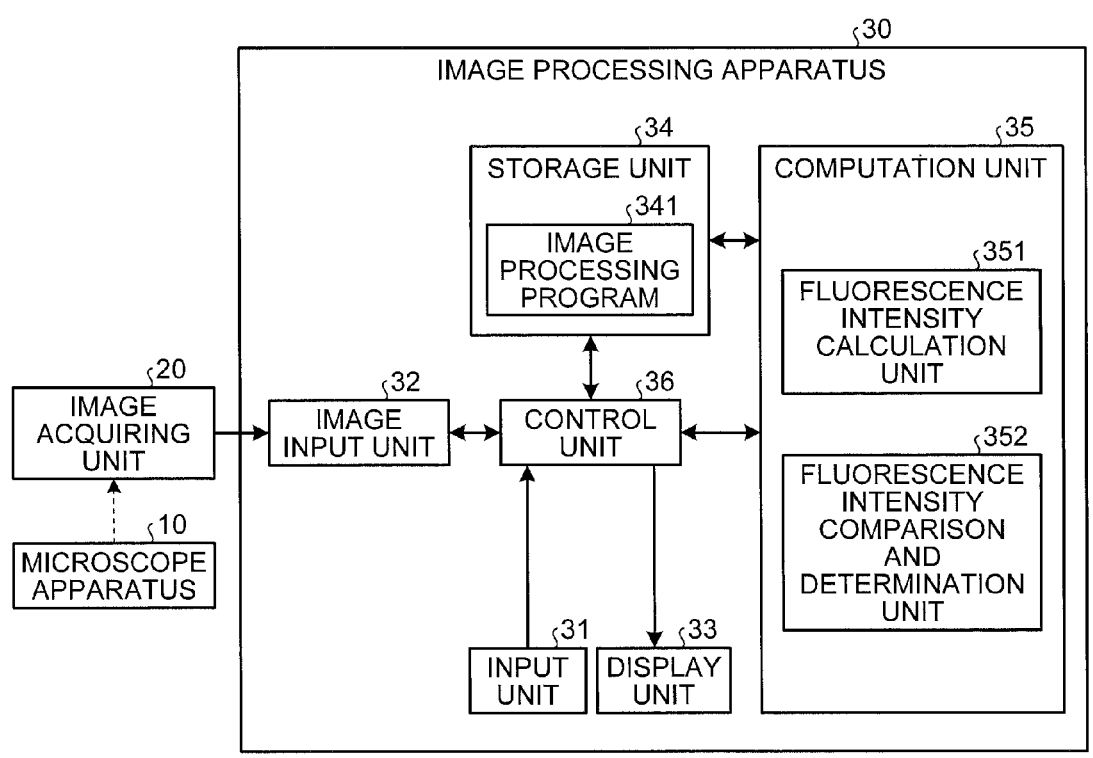
FIG. 1 is a block diagram illustrating a configuration of a microscope system according to a first embodiment of the present invention.

FIG. 1 is a block diagram illustrating a configuration of a microscope system according to a first embodiment of the present invention. As illustrated in FIG. 1, a microscope system 1 according to the first embodiment includes: a microscope apparatus 10; an image acquiring unit 20 that acquires an image (microscope image) of a specimen observed in the microscope apparatus 10; and an image processing apparatus 30 that processes the microscope image acquired by the image acquiring unit 20.

Figure 2:
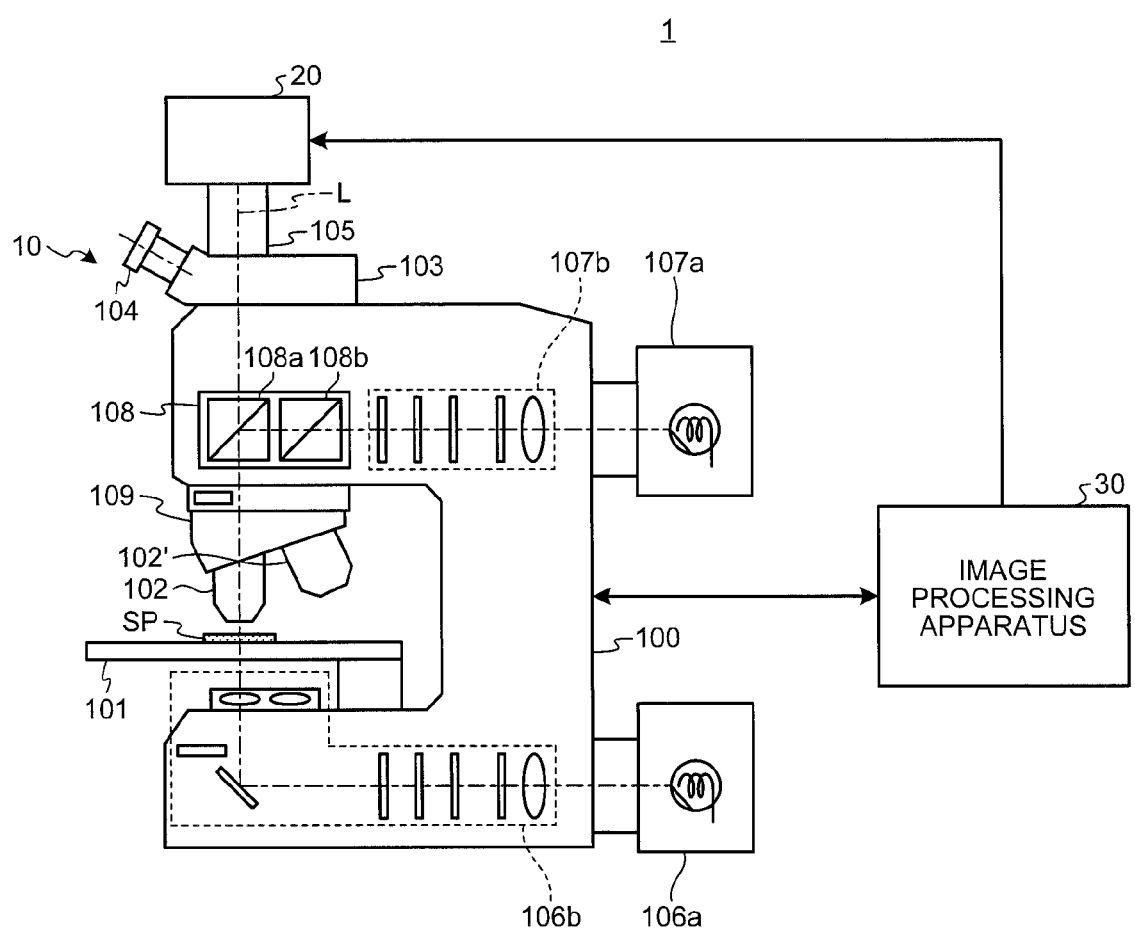
FIG. 2 is a schematic diagram illustrating an example of a configuration of a microscope apparatus illustrated in FIG. 1.

FIG. 2 is a schematic diagram conceptually illustrating a configuration of the microscope apparatus 10. As illustrated in FIG. 2, the microscope apparatus 10 includes: an arm unit 100 that is approximately C-shaped; a specimen stage 101 that is attached to the arm unit 100; an objective lens 102 that is arranged opposite to the specimen stage 101; a trinocular lens barrel unit 103 that is attached to the arm unit 100; an eyepiece unit 104 that is provided via the trinocular lens barrel unit 103; and an imaging lens unit 105 that is joined to the trinocular lens barrel unit 103. The image acquiring unit 20 is provided at an end portion of the imaging lens unit 105. Further, an illumination system, which is: a transmitted-light illumination light source 106a and a transmitted-light illumination optical system 106b; an epi-illumination light source 107a and an epi-illumination optical system 107b; and a cube unit 108 that interchangeably holds a plurality of optical cubes 108a and 108b, is provided in the arm unit 100.

The objective lens 102 is attached to a revolver 109 that is able to hold a plurality of objective lenses (for example, an objective lens 102') having magnifications different from one another. By rotating this revolver 109 and changing the objective lenses 102 and 102' opposite to the specimen stage 101, a magnification of the image imaged by the image acquiring unit 20 is able to be changed.

The trinocular lens barrel unit 103 branches observation light of a specimen SP incident from the objective lens 102, into a direction of the image acquiring unit 20 and a direction of the eyepiece unit 104. The eyepiece unit 104 is for a user to directly observe the specimen SP.

A zoom unit, which includes a plurality of zoom lenses and a drive unit (both not illustrated) that changes positions of these zoom lenses, is provided in the imaging lens unit 105. The zoom unit magnifies or reduces a target to be imaged within an imaging field by adjusting the positions of the zoom lenses.

The transmitted-light illumination optical system 106b includes various optical members (a collector lens, a filter unit, a field stop, a shutter, an aperture diaphragm, a condenser optical element unit, a top lens unit, and the like) that condense, and guide in a direction of an observation optical path L, transmitting illumination light emitted from the transmitted-light illumination light source 106a. On the other hand, the epi-illumination optical system 107b includes various optical members (a filter unit, a shutter, a field stop, an aperture diaphragm, and the like) that condense, and guide in the direction of the observation optical path L, epi-illumination light emitted from the epi-illumination light source 107a.

The cube unit 108 includes a plurality of optical cubes 108a and 108b inside thereof, and changes over, according to various microscopies, for example, transmitting bright field observation and fluorescence observation, the optical cubes to be arranged on the observation optical path L. For example, if fluorescence observation is performed in the microscope apparatus 10, an optical cube (fluorescence cube) is used, which is cubically combined of: an excitation filter that selectively transmits light (excitation light) of a particular wavelength band from the light emitted from the epi-illumination optical system 107b; a dichroic mirror that reflects the excitation light selected by the excitation filter and transmits fluorescence generated in the specimen SP; and an absorption filter that selectively transmits only light of a particular wavelength band from the fluorescence generated in the specimen SP.

The image acquiring unit 20 is realized by a multiband camera that includes an imaging element such as, for example, a CCD, and that is able to capture a color image having pixel levels (pixel values) in a plurality of mutually different wavelength bands (bands) among respective pixels. In the first embodiment, the image acquiring unit 20 used is a multiband camera, which is able to perform imaging in at least three bands at about 400 nm to about 900 nm ranging over from a visible region to a near infrared region. The image acquiring unit 20 receives light (observation light) that is emitted from the objective lens 102 and incident via the imaging lens unit 105, and generates and output to the image processing apparatus 30 image data corresponding to the observation light.

The image processing apparatus 30 includes: an input unit 31 that receives an input of an instruction or information with respect to the image processing apparatus 30; an image input unit 32 that is an interface to receive an input of the image of microscope output from the image acquiring unit 20; a display unit 33 that displays the image of microscope and other information; a storage unit 34; a computation unit 35 that performs specified image processing with respect to the image of microscope; and a control unit 36 that controls operations of each of these units and operations of the image acquiring unit 20.

The input unit 31 includes an input device such as a keyboard, various buttons, or various switches, and a pointing device such as a mouse or a touch panel, receives signals input via these devices, and inputs the received signals to the control unit 36.

The display unit 33 is realized by a display device such as, for example, a liquid crystal display (LCD), an electroluminescence (EL) display, or a cathode ray tube display, and displays various screens according to control signals output from the control unit 36.

The storage unit 34 is realized by: a semiconductor memory such as a flash memory that is rewritable, a RAM, or a ROM; or a hard disk which is built-in or connected via a data communication terminal, a recording medium such as an MO, a CD-R, or a DVD-R, as well as a reading device or the like that reads information recorded on that recording medium. The storage unit 34 stores therein the image data output from the image acquiring unit 20, various programs respectively executed by the computation unit 35 and the control unit 36, and various setting information. Specifically, the storage unit 34 stores therein an image processing program 341 that detects auto-fluorescence from the microscope image and determines fluorescent staining to be avoided to be used when performing fluorescence observation by superimposing a fluorescence labeled antibody on a non-fluorescence stained specimen based on the auto-fluorescence. Further, the storage unit 34 stores therein as information to be used upon execution of this image processing program 341, for example, information related to a commercially available fluorescent dye (a name of the fluorescent dye, a wavelength band of fluorescence emitted by the fluorescent dye, a center wavelength, a fluorescence intensity, an intensity spectrum of the fluorescence, or the like).

The computation unit 35 and the control unit 36 are realized, for example, by loading the various programs stored in the storage unit 34 into hardware such as a CPU.

The computation unit 35 detects, based on the image of microscope corresponding to the image data stored in the storage unit 34, auto-fluorescence emitted by the specimen (hereinafter, referred to as "non-fluorescence stained specimen") that has been subjected to non-fluorescent staining such as HE staining, and executes, based on this auto-fluorescence, image processing to determine a wavelength band of fluorescence superimposable or not superimposable when performing fluorescent observation by superimposing a fluorescence labeled antibody on the non-fluorescence stained specimen. In more detail, the computation unit 35 includes: a fluorescence intensity calculation unit 351, which is a characteristic amount calculation unit that calculates a fluorescence intensity that is characteristic amount of each of a plurality of microscope images; and a fluorescence intensity comparison and determination unit 352 that determines, based on a comparison result of comparing the fluorescence intensity of each microscope image with a specified threshold value, the wavelength band of the fluorescence superimposable or not superimposable.

Based on various data stored in the storage unit 34 and various information input through the input unit 31, the control unit 36 comprehensively controls operations of the whole microscope system 1 by transferring instructions and data to respective units of the microscope apparatus 10, the image acquiring unit 20, and the image processing apparatus 30.

The image processing apparatus 30 as described is realized by a general purpose apparatus such as, for example, a personal computer or a work station.

Figure 3:
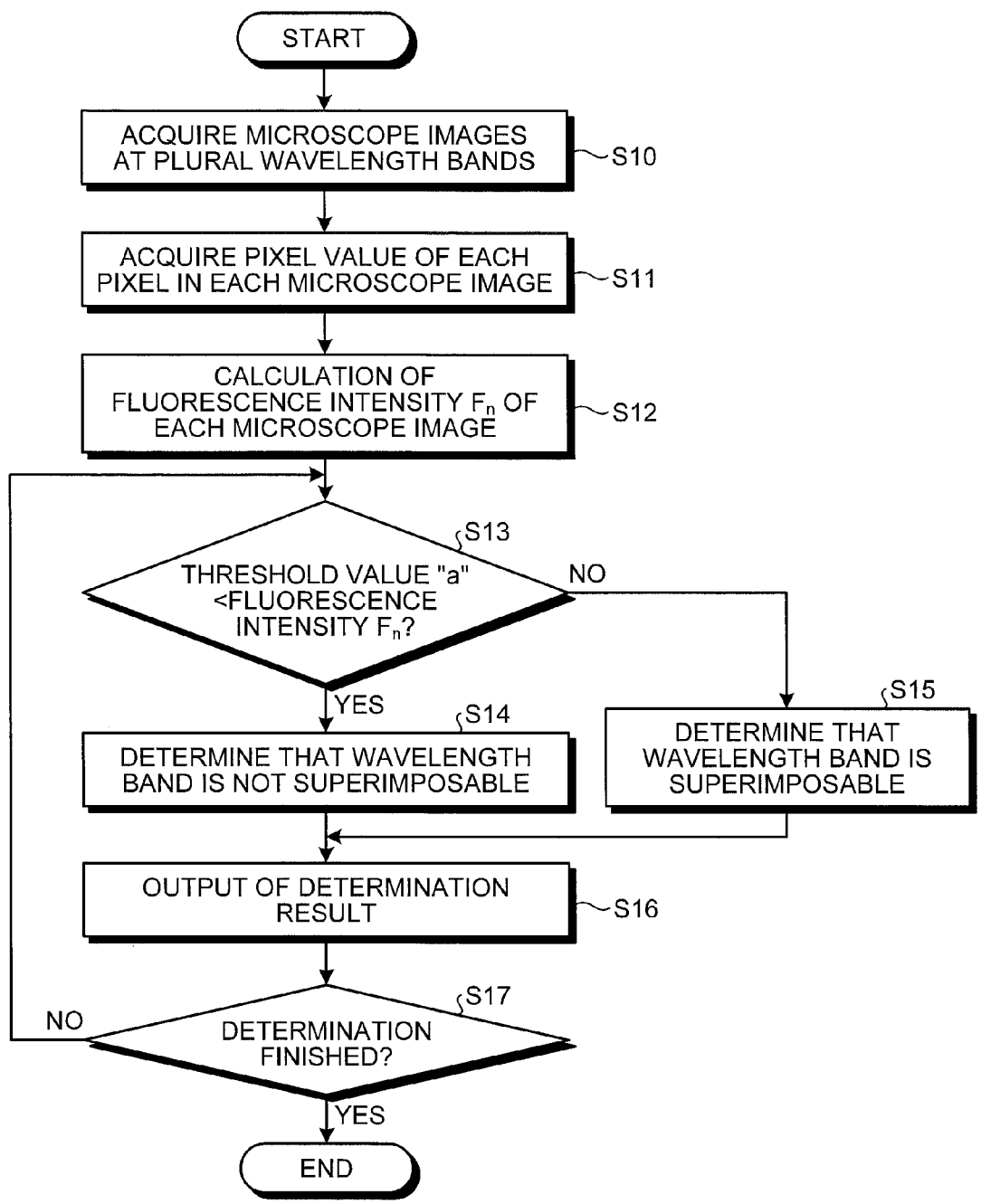
FIG. 3 is a flow chart illustrating operations of the microscope system illustrated in FIG. 1.

Next, the operations of the microscope system 1 are explained. FIG. 3 is a flow chart illustrating the operations of the microscope system 1. The microscope system 1 according to the first embodiment is for allowing a user, in order to suppress influence by auto-fluorescence emitted by a non-fluorescence stained specimen on detection of fluorescence emitted by a fluorescence labeled antibody when fluorescence observation is performed by superimposing the fluorescence labeled antibody on the non-fluorescence stained specimen: to comprehend a wavelength band at which the auto-fluorescence occurs in the non-fluorescence stained specimen before being stained with the fluorescence labeled antibody; and to select a fluorescent dye that generates fluorescence (hereinafter, also referred to as "superimposable fluorescence") of a wavelength band excluding the wavelength band of the auto-fluorescence.

At step S10, the microscope system 1 acquires a plurality of microscope images acquired by imaging, in a plurality of mutually different wavelength bands, a non-fluorescence stained specimen placed on the specimen stage 101. In more detail, a specified fluorescent cube (for example, the optical cube 108$a$) is arranged on the observation optical axis L of the microscope apparatus 10 and the epi-illumination light is irradiated to the non-fluorescence stained specimen via the epi-illumination optical system 107$b$. The image acquiring unit 20 performs imaging at a plurality of wavelength bands where detection of fluorescent light according to the fluorescent cube is possible and acquires a plurality of microscope images. Such an operation is performed more than once while changing to a fluorescent cube of a type having a different wavelength band of fluorescent light. The image data of the microscope image at each wavelength band acquired as a result of that are output to the image processing apparatus 30 and stored in the storage unit 34 via the image input unit 32.

Figure 4:
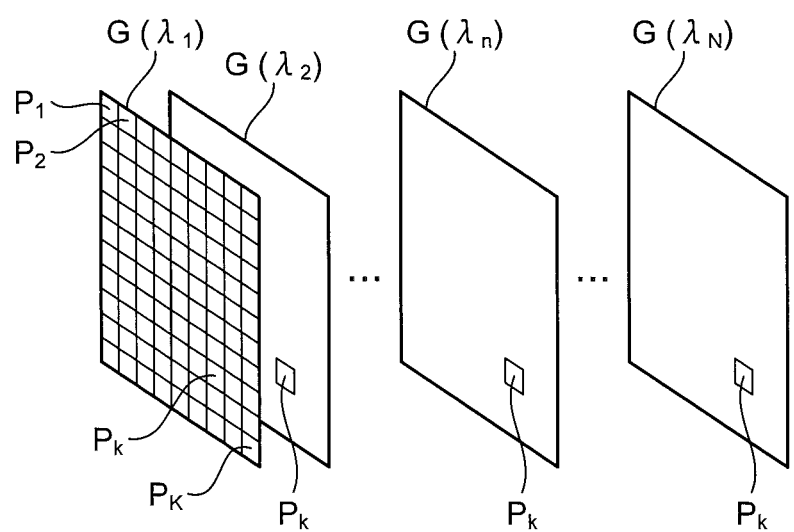
FIG. 4 is a schematic diagram conceptionally illustrating a series of microscope images acquired for respective wavelength bands.

At step S11, the fluorescence intensity calculation unit 351 acquires a pixel value of each pixel in each microscope image, based on the image data stored in the storage unit 34. Specifically, the fluorescence intensity calculation unit 351 acquires, as illustrated in FIG. 4, each pixel $P_k$ (k=1 to K) from a microscope image $G(\lambda_n)$ of each wavelength band having a center wavelength at a wavelength $\lambda_n$ (n=1 to N).

At step S12, the fluorescence intensity calculation unit 351 calculates, for each microscope image $G(\lambda_n)$, characteristic amount, which is a fluorescence intensity $F_n$ representing auto-fluorescence. The fluorescence intensity $F_n$ is calculated from a quantity $x_{(n, k)}$ based on a pixel value of a pixel in the microscope image $G(\lambda_n)$. The quantity $x_{(n, k)}$ based on the pixel value here may be a pixel value as is, or a value (for example, a luminance) acquired by subjecting a specified computation process to the pixel value. Further, a maximum value, a minimum value, a mode value, an average value, a total value, or the like of the quantity $x_{(n, k)}$ based on the pixel value is used as the fluorescence intensity $F_n$. Since each microscope image $G(\lambda_n)$ is imaged for each different wavelength band, the fluorescence intensity (intensity of auto-fluorescence) of each wavelength band is calculated.

In the present embodiment, the following step S13 is executed next, but the process may be ended after calculating the fluorescence intensity as the characteristic amount.

This is because a person with experience is able to determine whether the fluorescence labeled antibody is superimposable or not, once the value of the intensity of the auto-fluorescence is known.

At step S13, the fluorescence intensity comparison and determination unit 352 compares the fluorescence intensity $F_n$ of the microscope image $G(\lambda_n)$ with a specified threshold value "a" that has been set beforehand. This threshold value "a" is set based on, for example, intensity information of known fluorescence (for example, fluorescence generated by a commercially available fluorescent dye) on which the storage unit 34 holds information.

If the fluorescence intensity $F_n$ is greater than the threshold value "a" (step S13: Yes), the fluorescence intensity comparison and determination unit 352 determines that the wavelength band of the microscope image $G(\lambda_n)$, which is the target to be determined, is not appropriate (not superimposable) as the wavelength band to be superimposed with the fluorescence when performing fluorescence observation in which the fluorescence labeled antibody is superimposed on the non-fluorescence stained specimen, because at that wavelength band of the microscope image $G(\lambda_n)$, the auto-fluorescence is intense and that wavelength band of the microscope image $G(\lambda_n)$ is a wavelength band that influences the fluorescence labeled antibody (step S14). In other words, it is not appropriate to label an antibody using a fluorescent dye that generates fluorescence of such a wavelength band and to superimpose it on a non-fluorescence stained specimen. Hereinafter, such a wavelength band will be referred to as "wavelength band of non-superimposable fluorescence" or simply as "non-superimposable wavelength band".

If the fluorescence intensity $F_n$ is equal to or less than the threshold value "a" (step S13: No), it is determined that the wavelength band of the microscope image $G(\lambda_n)$, which is the target to be determined, is appropriate (superimposable) as the wavelength band to be superimposed with the fluorescence when performing fluorescence observation in which the fluorescence labeled antibody is superimposed on the non-fluorescence stained specimen, because at that wavelength band of the microscope image $G(\lambda_n)$, the auto-fluorescence is weak or there is not auto-fluorescence and that wavelength band of the microscope image $G(\lambda_n)$ is a wavelength band that does not influence the fluorescence labeled antibody (step S15). In other words, it is possible to perform fluorescence observation by labeling an antibody using a fluorescent dye that emits fluorescence of such a wavelength band and superimposing it on a non-fluorescence stained specimen. Hereinafter, such a wavelength band will be referred to as "wavelength band of superimposable fluorescence" or simply as "superimposable wavelength band".

At step S16, the computation unit 35 outputs a result of the determination of step S14 or S15 to the control unit 36. Accordingly, the control unit 36 stores the result of the determination in the storage unit 34 and causes the display unit 33 to display the result of the determination.

At step S17, the control unit 36 determines whether the determination with respect to all of the microscope images $G(\lambda_n)$ has finished or not. If the determination with respect to all of the microscope images $G(\lambda_n)$ has finished (step S17: Yes), the operations of the microscope system 1 are ended. If a microscope image $G(\lambda_n)$ for which the determination has not been made still remains (step S17: No), the operations of the microscope system 1 return to step S13.

As described above, according to the first embodiment, by comparing the fluorescence intensity of the microscope image acquired by imaging the non-fluorescence stained specimen at each wavelength band with the specified threshold value, a wavelength band having a high fluorescence intensity is determined. Therefore, by referring to this determination result, a user is able to comprehend the wavelength band of the auto-fluorescence emitted by the non-fluorescence stained specimen and to readily select a fluorescent dye to stain the fluorescence labeled antibody to be superimposed on the non-fluorescence stained specimen. Accordingly, the user is able to obtain an accurate observation result having decreased influence of auto-fluorescence when performing fluorescence observation on a specimen by superimposing a fluorescence labeled antibody on a non-fluorescence stained specimen.

Further, in the first embodiment, because the possibility and impossibility of using the fluorescence at each wavelength band is determined by the comparatively easy process of comparing the fluorescence intensity calculated from the microscope image of each wavelength band with the threshold value, a determination result with respect to a wide range of wavelength band is able to be acquired by a simple and quick process.

Further, according to the first embodiment, because the multiband camera of three bands or more is used as the image acquiring unit 20, a wavelength band where auto-fluorescence occurs is able to be accurately determined.

Further, according to the first embodiment, because the multiband camera, which is able to perform imaging at about 400 nm to about 900 nm ranging from the visible region to the near infrared region, is used, even if auto-fluorescence is occurring over a wide band including the visible region, a user is able to check the presence or absence of auto-fluorescence in the wavelength band of near infrared fluorescence and to select a fluorescent dye having small influence of auto-fluorescence.

Second Embodiment

Next, a second embodiment of the present invention will be described.

Figure 5:
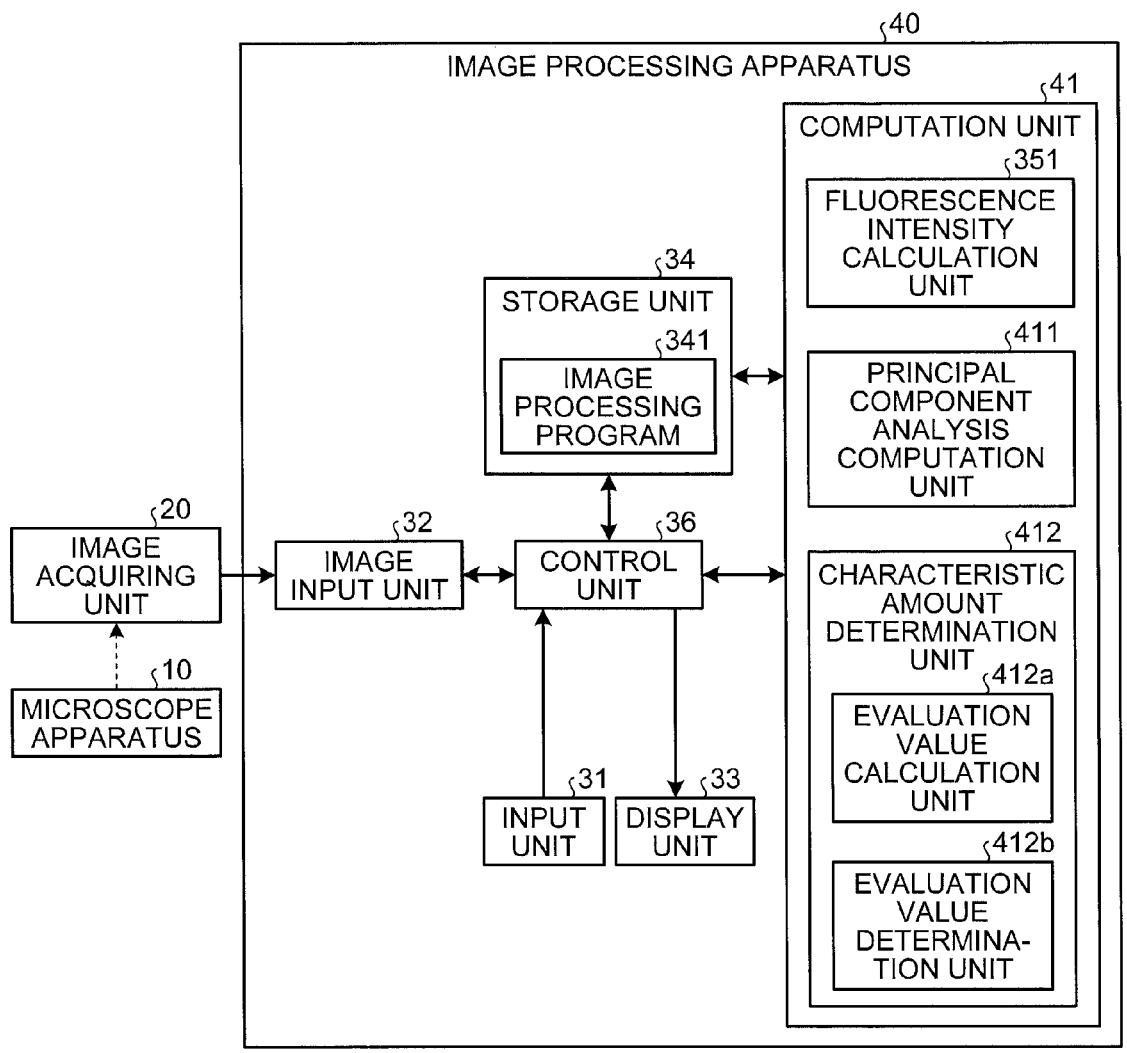
FIG. 5 is a block diagram illustrating a configuration of a microscope system according to a second embodiment of the present invention.

FIG. 5 is a block diagram illustrating a configuration of a microscope system according to a second embodiment. As illustrated in FIG. 5, a microscope system 2 according to the second embodiment has, instead of the image processing apparatus 30 illustrated in FIG. 1, an image processing apparatus 40 having a computation unit 41.

The computation unit 41 includes, instead of the fluorescence intensity comparison and determination unit 352 illustrated in FIG. 1: a principal component analysis computation unit 411, which is a characteristic amount calculation unit that calculates, based on a series of microscope images $G(\lambda_n)$, characteristic amount of auto-fluorescence emitted by a non-fluorescence stained specimen; and a characteristic amount determination unit 412 that determines, based on a correlation between the characteristic amount of the auto-fluorescence and characteristic amount of known fluorescence (for example, fluorescence emitted by a commercially available fluorescent dye), whether the known fluorescence is usable or not as fluorescence in superimposing a fluorescence labeled antibody on the non-fluorescence stained specimen to perform fluorescence observation.

Of these, the characteristic amount determination unit 412 includes: an evaluation value calculation unit 412a that calculates an evaluation value using the characteristic amount of the auto-fluorescence and the characteristic amount of the known fluorescence; and an evaluation value determination unit 412b that determines whether or not the known fluorescence is usable based on the evaluation value.

A configuration of the image processing apparatus 40 other than the principal component analysis computation unit 411 and the characteristic amount determination unit 412, and a configuration of the whole microscope system are similar to those of the first embodiment.

Next, a principle of a computation process in the second embodiment is described.

Figure 6:
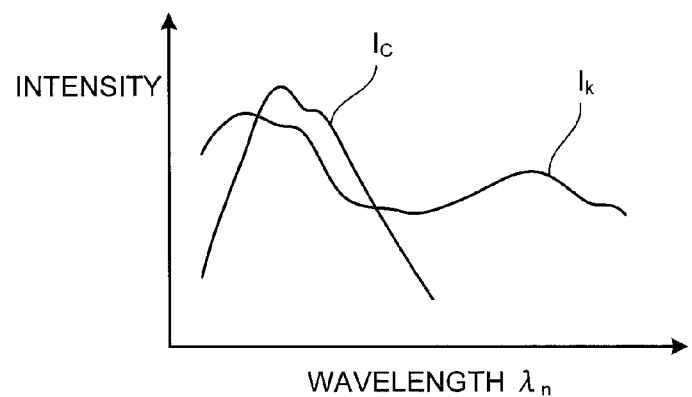
FIG. 6 is a graph illustrating an intensity spectrum for corresponding pixels among the series of microscope images illustrated in FIG. 4 and an intensity spectrum of known fluorescence.

In FIG. 6, a waveform (intensity spectrum) $I_k$ acquired by plotting intensities of light at pixels $P_k$ corresponding to one another among the series of microscope images $G(\lambda_n)$ is overlapped with an intensity spectrum $I_c$ of known fluorescence (for example, fluorescence emitted by a commercially available fluorescent dye like Cy3). In FIG. 6, a horizontal axis represents wavelength $\lambda_n$ and a vertical axis represents intensity of light. The intensity of light at each pixel $P_k$ is calculated by converting a pixel value through specified computation.

If the intensity spectrum $I_k$ determined according to the wavelength is detected from the series of microscope images $G(\lambda_n)$, the intensity spectrum $I_k$ may be considered to correspond to the auto-fluorescence generated by the non-fluorescence stained specimen. Thus, if an intensity spectrum $I_k$ having a strong correlation with the intensity spectrum of the known fluorescence is detected, there is a possibility that the known fluorescence is influenced by the auto-fluorescence. Accordingly, in the second embodiment, the intensity spectrum $I_k$ corresponding to each pixel $P_k$ is treated as characteristic amount of the auto-fluorescence generated by the non-fluorescence stained specimen, and usability or non-usability of the fluorescence in each wavelength band is determined based on this intensity spectrum $I_k$.

The intensity spectrum $I_k$ is acquired as many as the number of pixels of the microscope image $G(\lambda_n)$. Therefore, in the second embodiment, by executing principal component analysis computation, only an intensity spectrum $I_k$ to be noted is extracted from "K" intensity spectra $I_k$.

Figure 7:
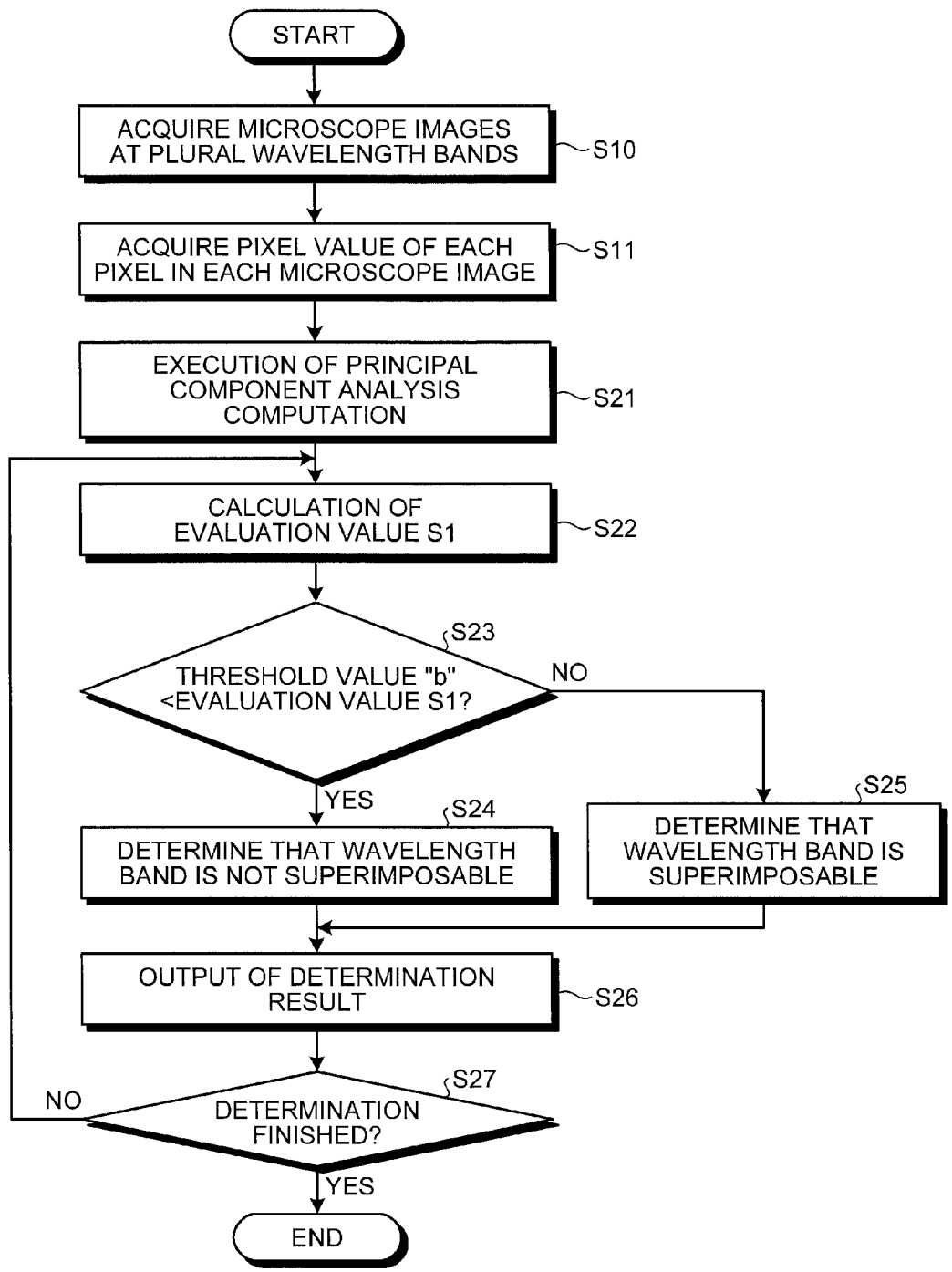
FIG. 7 is a flow chart illustrating operations of the microscope system according to the second embodiment of the present invention.

Next, the operations of the microscope system 2 are described. FIG. 7 is a flow chart illustrating the operations of the microscope system 2. Operations of steps S10 and S11 illustrated in FIG. 7 are common with the first embodiment.

At step S21 following step S11, the principal component analysis computation unit 411 executes principal component analysis computation with respect to a quantity $x_{(n, k)}$ based on a pixel value of each pixel $P_k$ (k=1 to K) in a series of microscope images $G(\lambda_n)$ (n=1 to N) calculated by the fluorescence intensity calculation unit 351.

Specifically, as represented by the following Equation (1), the principal component analysis computation unit 411 generates, for each pixel $P_k$, a characteristic vector $X_k$ having a component that is the quantity $x_{(n, k)}$ based on the pixel value (k=1 to K).

$$X_k = (x_{(1,k)}, x_{(2,k)}, \ldots, x_{(N,K)})^t \qquad (1)$$

In Equation (1), the "t" of the characteristic vector indicates a transposed vector. This characteristic vector $X_k$ corresponds to the intensity spectrum $I_k$ illustrated in FIG. 6.

In more detail, each characteristic vector $X_k$ is represented as follows.

$$X_1 = \begin{pmatrix} x_{(1,1)} \\ x_{(2,1)} \\ \vdots \\ x_{(n,1)} \\ \vdots \\ x_{(N,1)} \end{pmatrix}, X_2 = \begin{pmatrix} x_{(1,2)} \\ x_{(2,2)} \\ \vdots \\ x_{(n,2)} \\ \vdots \\ x_{(N,2)} \end{pmatrix}, \ldots, X_k = \begin{pmatrix} x_{(1,k)} \\ x_{(2,k)} \\ \vdots \\ x_{(n,k)} \\ \vdots \\ x_{(N,k)} \end{pmatrix}, \ldots, X_K = \begin{pmatrix} x_{(1,K)} \\ x_{(2,K)} \\ \vdots \\ x_{(n,K)} \\ \vdots \\ x_{(N,K)} \end{pmatrix}$$

Further, the principal component analysis computation unit 411 calculates an average vector "M" having a component that is an average value for each pixel $P_k$ of the quantity $x_{(n, k)}$ based on the pixel value, as represented by the next Equation (2).

$$M = \frac{1}{N} \begin{pmatrix} x_{(1,1)} + x_{(2,1)} + \ldots + x_{(n,1)} + \ldots + x_{(N,1)} \\ x_{(1,2)} + x_{(2,2)} + \ldots + x_{(n,2)} + \ldots + x_{(N,2)} \\ \vdots \\ x_{(1,k)} + x_{(2,k)} + \ldots + x_{(n,k)} + \ldots + x_{(N,k)} \\ \vdots \\ x_{(1,K)} + x_{(2,K)} + \ldots + x_{(n,K)} + \ldots + x_{(N,K)} \end{pmatrix} = \begin{pmatrix} m_1 \\ m_2 \\ \vdots \\ m_K \end{pmatrix} \qquad (2)$$

Further, the principal component analysis computation unit 411 calculates a variance-covariance matrix "S" represented by the next Equation (3) by using the characteristic vector $X_k$ and the average vector "M".

$$S = \frac{1}{N} \cdot \begin{pmatrix} \sum_{j=1}^{K}(x_{(1,j)}-m_j)(x_{(1,j)}-m_j), & \ldots, & \sum_{j=1}^{K}(x_{(1,j)}-m_j)(x_{(n,j)}-m_j), & \ldots, & \sum_{j=1}^{K}(x_{(1,j)}-m_j)(x_{(N,j)}-m_j) \\ \sum_{j=1}^{K}(x_{(2,j)}-m_j)(x_{(1,j)}-m_j), & \ldots, & \sum_{j=1}^{K}(x_{(2,j)}-m_j)(x_{(n,j)}-m_j), & \ldots, & \sum_{j=1}^{K}(x_{(2,j)}-m_j)(x_{(N,j)}-m_j) \\ \vdots & & \vdots & & \vdots \\ \sum_{j=1}^{K}(x_{(n,j)}-m_j)(x_{(1,j)}-m_j), & \ldots, & \sum_{j=1}^{K}(x_{(n,j)}-m_j)(x_{(n,j)}-m_j), & \ldots, & \sum_{j=1}^{K}(x_{(n,j)}-m_j)(x_{(N,j)}-m_j) \\ \vdots & & \vdots & & \vdots \\ \sum_{j=1}^{K}(x_{(N,j)}-m_j)(x_{(1,j)}-m_j), & \ldots, & \sum_{j=1}^{K}(x_{(N,j)}-m_j)(x_{(n,j)}-m_j), & \ldots, & \sum_{j=1}^{K}(x_{(N,j)}-m_j)(x_{(N,j)}-m_j) \end{pmatrix} \qquad (3)$$

The principal component analysis computation unit 411 calculates an eigenvector "u" satisfying $Su=\lambda u$, for this variance-covariance matrix "S". This eigenvector "u" is used as the characteristic amount (characteristic vector) of the auto-fluorescence emitted by the non-fluorescence stained specimen.

Subsequently, at step S22, the evaluation value calculation unit 412a calculates an evaluation value S1 given by the next Equation (4), by using the eigenvector "u".

$$S1 = \left| \frac{\vec{v} \cdot \vec{u}}{|\vec{v}||\vec{u}|} \right| \quad (4)$$

In Equation (4), a vector "v" is a characteristic vector of known fluorescence, and has a component that is a fluorescence intensity at each wavelength $\lambda_n$ acquired from the intensity spectrum $I_c$ of the fluorescence as illustrated in FIG. 6, for example. Such a vector "v" is sequentially generated from the information related to the fluorescent dyes stored in the storage unit 34.

As represented by Equation (4), the evaluation value S1 is an absolute value of a value acquired by normalizing an inner product of the vector "v" and the eigenvector "u". If a plurality of eigenvectors are calculated at step S21, in Equation (4), the eigenvectors are sequentially substituted in the one vector "v" and a plurality of evaluation values S1 are calculated.

Subsequently, at step S23, the evaluation value determination unit 412b compares the evaluation value S1 with a specified threshold value "b" that is set beforehand. If a plurality of evaluation values S1 are calculated at step S22, determination with respect to each evaluation value S1 is performed.

Figure 8:
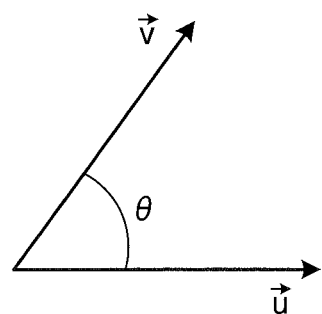
FIG. 8 is a diagram illustrating a quantity represented by an evaluation value S1.

As illustrated in FIG. 8, a correlation between the eigenvector "u" and the vector "v" becomes higher as an angle θ between these becomes smaller, that is, as a value of cos θ becomes larger. In this case, influence by the auto-fluorescence on the known fluorescence becomes large. Thus, if the evaluation value S1 is greater than the threshold value "b" (step S23: Yes), the evaluation value determination unit 412b determines that the wavelength band in which that known fluorescence is distributed is not superimposable (step S24). On the contrary, if the evaluation value S1 is equal to or less than the threshold value "b" (step S23: No), it is determined that that wavelength band is superimposable (step S25). If a plurality of evaluation values S1 are calculated and if at least one evaluation value S1 greater than the threshold value "b" is present among them, that wavelength band is determined to be not superimposable.

At step S26, the computation unit 41 outputs a result of the determination of step S24 or S25 to the control unit 36. Accordingly, the control unit 36 stores the result of the determination in the storage unit 34 and causes the display unit 33 to display the result of the determination. A format of the display may be a format of displaying usability or non-usability with respect to all wavelength bands $\lambda_1$ to $\lambda_N$, or a format of displaying only the wavelength band determined to be superimposable, or a format of displaying a name of a fluorescent dye that emits the fluorescence distributed in the wavelength band determined to be superimposable.

At step S27, the control unit 36 determines whether the determination with respect to all of fluorescence on which the storage unit 34 holds information has finished or not. If the determination with respect to all of the fluorescence has finished (step S27: Yes), the operations of the microscope system 2 are ended. If fluorescence for which the determination has not been made still remains (step S27: No), the operations of the microscope system 2 return to step S22.

As described above, in the second embodiment, because computation using the quantities based on the pixel values of all of the pixels in the series of the microscope images is performed, a more highly accurate determination result is obtainable. Therefore, based on this determination result, a user is able to more infallibly select a fluorescent dye having small influence of the auto-fluorescence. As a result, when performing fluorescence observation on a specimen acquired by superimposing a fluorescence labeled antibody on a non-fluorescence stained specimen, the user is able to obtain a more accurate observation result of which the influence by the auto-fluorescence has been suppressed.

Third Embodiment

Next, a third embodiment of the present invention will be described.

A configuration of a microscope system according to the third embodiment is similar to that illustrated in FIG. 5 and contents of operations in the characteristic amount determination unit 412 are different from those of the second embodiment.

Figure 9:
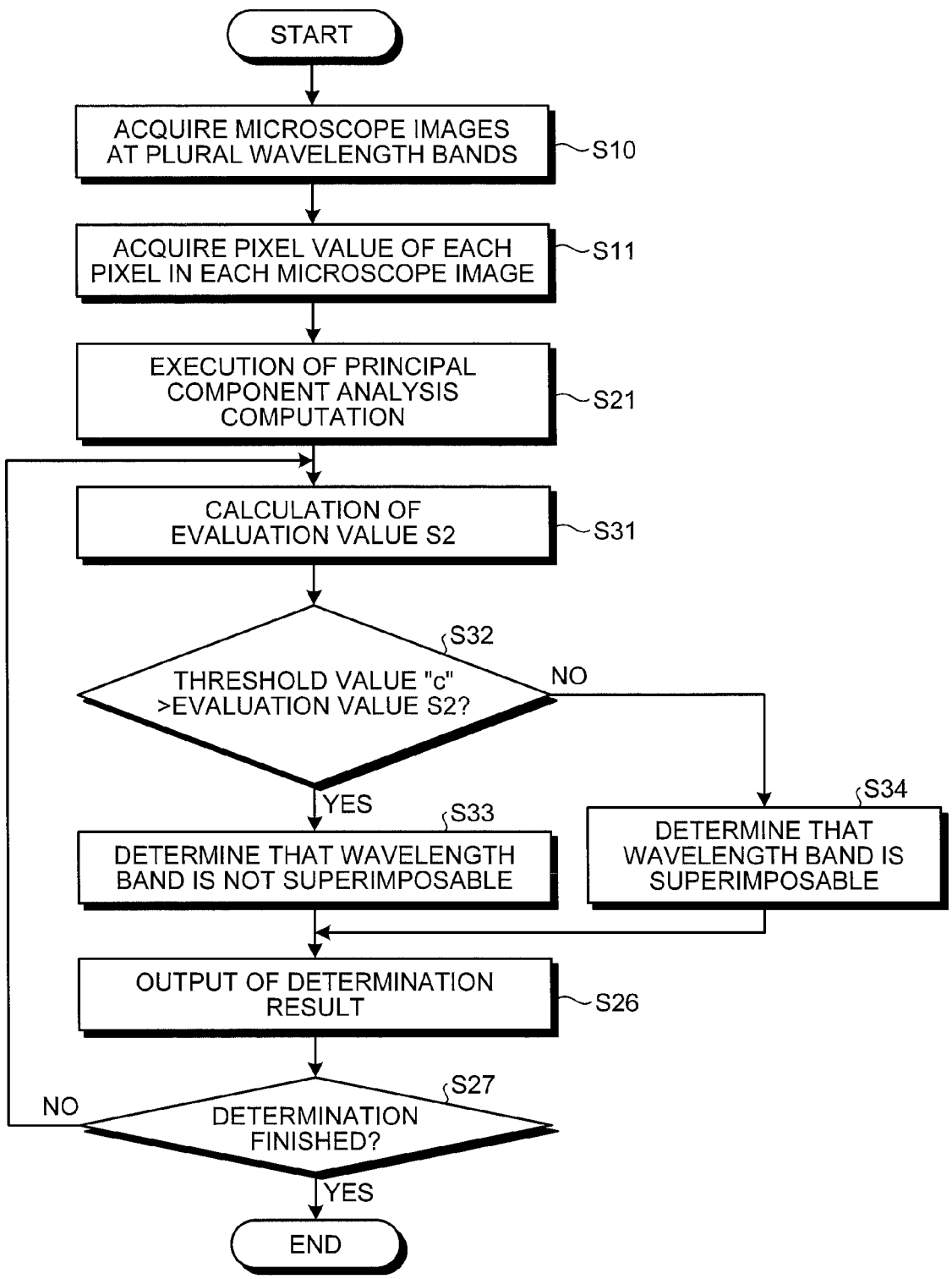
FIG. 9 is a flow chart illustrating operations of a microscope system according to a third embodiment of the present invention.

FIG. 9 is a flow chart illustrating the operations of the microscope system according to the third embodiment. As illustrated in FIG. 9, of the operations of the microscope system according to the third embodiment, the operations in steps S10, S11, S21, and S26 to S27 are common with those of the second embodiment.

At step S31 following step S21, the evaluation value calculation unit 412a calculates an evaluation value S2 given by the following Equation (5) using the eigenvector "u" calculated as the characteristic amount.

$$S2 = \left| \vec{v} - \frac{\vec{v} \cdot \vec{u}}{|\vec{v}||\vec{u}|} \cdot \vec{u} \right|^2 \quad (5)$$

In Equation (5), the vector "v" is a characteristic vector of known fluorescence and has a component that is an intensity at each wavelength $\lambda_n$. Such vectors "v" are sequentially generated from the information related to the fluorescent dyes stored in the storage unit 34.

As represented by Equation (5), the evaluation value S2 is equivalent to an inner product between difference vectors of: a vector acquired by projecting the eigenvector "u" in a direction of the vector "v"; and the vector "v".

If a plurality of eigenvectors are calculated at step S31, in Equation (5), the eigenvectors are sequentially substituted in the one vector "v" and a plurality of evaluation values S2 are calculated.

Subsequently, at step S32, the evaluation value determination unit 412b compares the evaluation value S2 with a specified threshold value "c" that is set beforehand. If a plurality of evaluation values S2 are calculated at step S31, determination with respect to each evaluation value S2 is performed.

Figure 10:
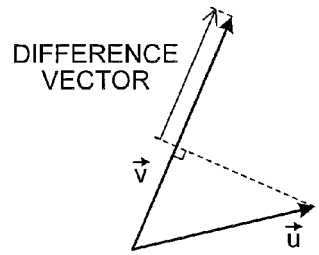
FIG. 10 is a diagram illustrating a quantity represented by an evaluation value S2.

As illustrated in FIG. 10, a correlation between the eigenvector "u" and the vector "v" becomes higher as a difference between them becomes smaller. That is, the influence of the auto-fluorescence on the known fluorescence becomes larger. Thus, if the evaluation value S2 is smaller than the threshold value "c" (step S32: Yes), the evaluation value determination unit 412b determines that the wavelength band in which that known fluorescence is distributed is not superimposable (step S33). On the contrary, if the evaluation value S2 is equal to or greater than the threshold value "c", the evaluation value determination unit 412b determines that the wavelength band is superimposable (step S34). Operations after that are similar to those of the second embodiment.

As described above, according to the third embodiment, based on an evaluation value more truly representing a correlation between an eigenvector "u" that is a characteristic vector of auto-fluorescence and a characteristic vector "v" of known fluorescence, determination on usability or non-usability of a wavelength band in which the known fluorescence is distributed is performed, and thus based on a result of this determination, a user is able to readily and infallibly select a fluorescent dye having a small influence by the auto-fluorescence.

Fourth Embodiment

Next, a fourth embodiment of the present invention will be described.

Figure 11:
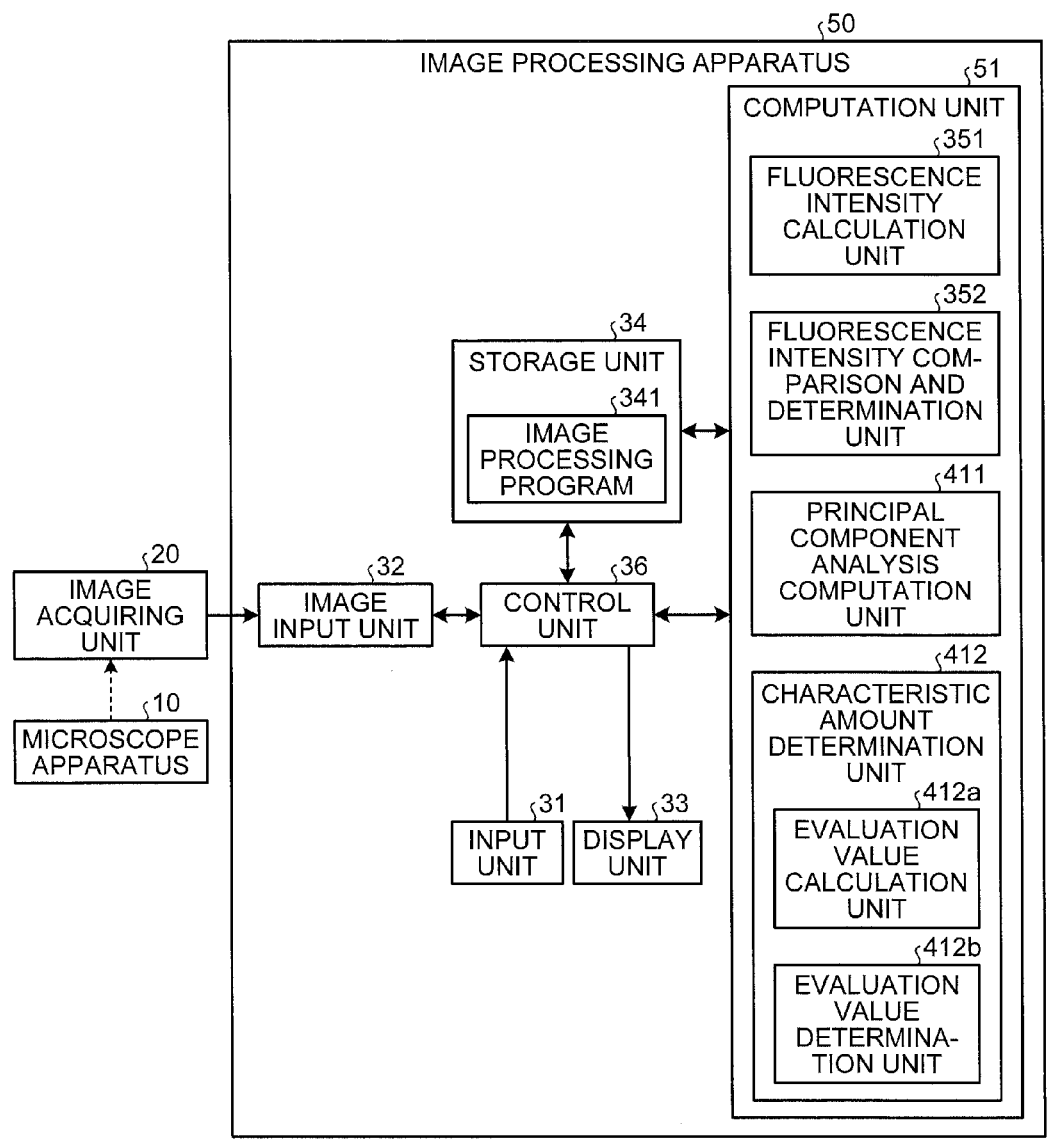
FIG. 11 is a block diagram illustrating a configuration of a microscope system according to a fourth embodiment of the present invention.

FIG. 11 is a block diagram illustrating a configuration of a microscope system according to a fourth embodiment. As illustrated in FIG. 11, a microscope system 4 according to the fourth embodiment has, instead of the image processing apparatus 30 illustrated in FIG. 1, an image processing apparatus 50 having a computation unit 51.

The computation unit 51 includes, in addition to the configuration of the computation unit 35 illustrated in FIG. 1, a principal component analysis computation unit 411 and a characteristic amount determination unit 412. Operations of these principal component analysis computation unit 411 and characteristic amount determination unit 412 are similar to those described in the second embodiment.

Figure 12:
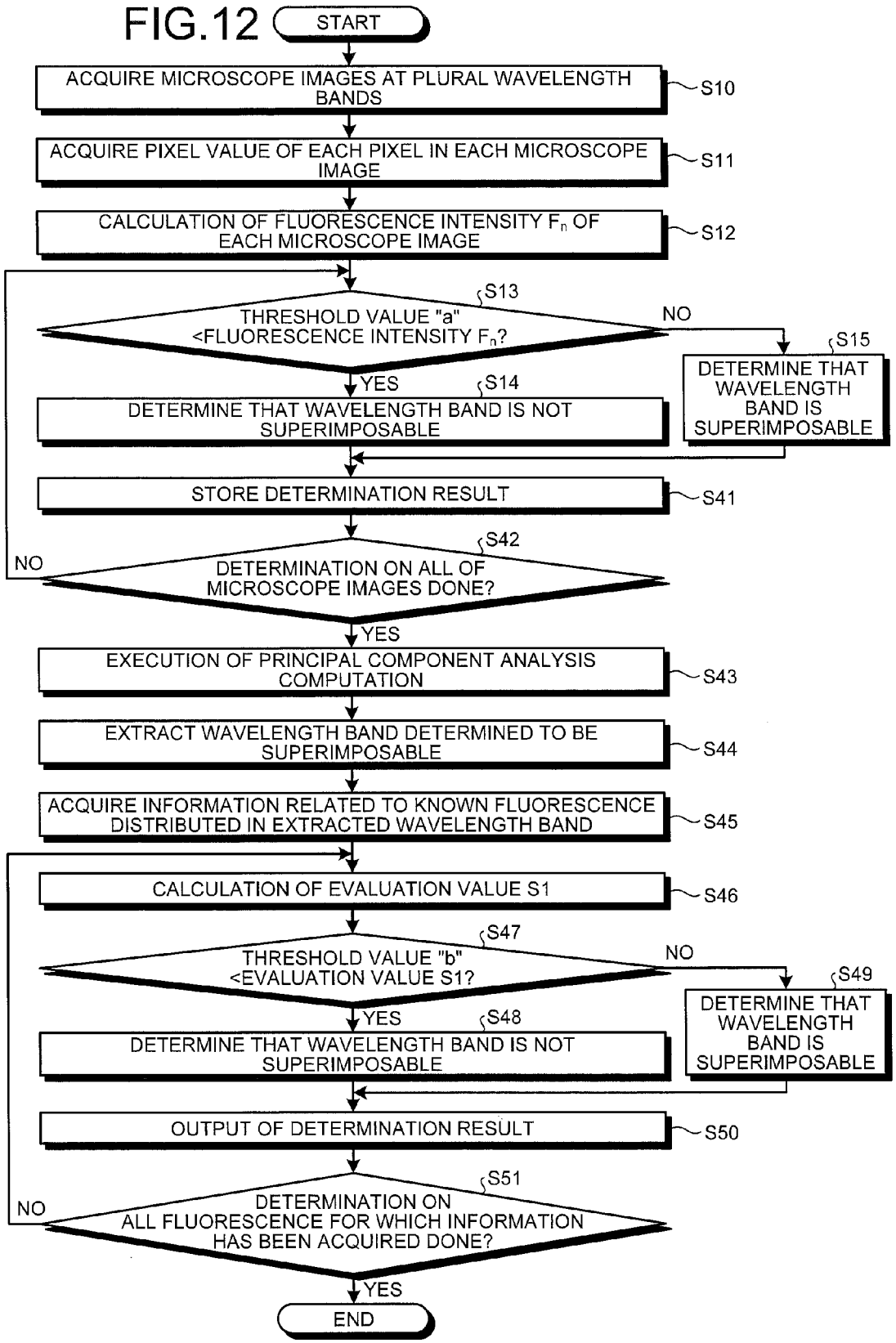
FIG. 12 is a flow chart illustrating operations of the microscope system illustrated in FIG. 11.

Next, the operations of the microscope system 4 are described. FIG. 12 is a flow chart illustrating the operations of the microscope system 4. Operations of steps S10 to S15 illustrated in FIG. 12 are common with the first embodiment.

At step S41 following steps S14 or S15, the computation unit 51 outputs a result of the determination and causes the storage unit 34 to temporarily store the result of the determination.

At step S42, the computation unit 51 determines whether the determination with respect to all of the microscope images $G(\lambda_n)$ has been made or not. If there is any microscope image $G(\lambda_n)$ for which the determination has not been made remaining (step S42: No), the operations return to step S13.

If the determination on all of the microscope images $G(\lambda_n)$ has finished (step S42: Yes), the principal component analysis computation unit 411 executes principal component analysis computation with respect to a quantity $x_{(n, k)}$ based on a pixel value of a pixel $P_k$ in the series of microscope images $G(\lambda_n)$, and calculates an eigenvector "u" that is a characteristic vector of the auto-fluorescence (step S43). Details of a method of calculating the eigenvector "u" are similar to those described in the second embodiment.

At step S44, the computation unit 51 extracts information of a wavelength band determined to be superimposable in step S15 from the storage unit 34.

At step S45, the computation unit 51 acquires from the storage unit 34 information related to known fluorescence (for example, fluorescence emitted by a commercially available fluorescent dye) distributed in the wavelength band extracted in step S44.

At step S46, the evaluation value calculation unit 412a calculates an evaluation value S1 given by Equation (4) by using the eigenvector "u" calculated in step S43 and the characteristic vector "v" generated from the information related to the known fluorescence acquired in step S45. If a plurality of eigenvectors are calculated at step S43, in Equation (4), the eigenvectors are sequentially substituted in the one vector "v" and a plurality of evaluation values S1 are calculated.

At step S47, the evaluation value determination unit 412b compares the evaluation value S1 with a specified threshold value "b" that is set beforehand. If a plurality of evaluation values S1 are calculated at step S46, determination with respect to each evaluation value S1 is performed.

If the evaluation value S1 is greater than the threshold value "b" (step S47: Yes), the evaluation value determination unit 412b determines that a wavelength band in which that known fluorescence is distributed is not superimposable (step S48). On the contrary, if the evaluation value S1 is equal to or less than the threshold value "b" (step S47: No), the evaluation value determination unit 412b determines that the wavelength band is superimposable (step S49). If a plurality of evaluation values S1 are calculated and at least one evaluation value S1 greater than the threshold value "b" is present among them, that wavelength band is determined to be not superimposable.

At step S50, the computation unit 51 outputs a result of the determination of step S14, and step S48 or S49. Accordingly, the control unit 36 stores the result of the determination in the storage unit 34 and causes that display unit 33 to display the result of the determination. A format of the display may be a format of displaying usability or non-usability with respect to all wavelength bands $\lambda_1$ to $\lambda_N$, or a format of displaying only the wavelength band determined to be superimposable, or a format of displaying a name of a fluorescent dye that emits the fluorescence distributed in the wavelength band determined to be superimposable.

At step S51, the control unit 36 determines whether the determination with respect to all of fluorescence for which the information has been acquired in step S45 has finished or not. If the determination with respect to all of the fluorescence has finished (step S51: Yes), the operations of the microscope system 4 are ended. If fluorescence for which the determination has not been made still remains (step S51: No), the operations of the microscope system 4 return to step S46.

As described above, in the fourth embodiment, after excluding, based on a fluorescence intensity of each microscope image, a wavelength band having a large intensity of auto-fluorescence, usability or non-usability of each wavelength band is determined, for remaining wavelength bands, based on a correlation between an eigenvector calculated by principal component analysis and a characteristic vector of known fluorescence. Therefore, improvement in efficiency of the computation process and obtainment of a highly accurate determination result become possible.

In the above fourth embodiment, instead of the evaluation value S1 given by Equation (4), the evaluation value S2 given by Equation (5) may be calculated to perform the determination.

Fifth Embodiment

Next, a fifth embodiment of the present invention will be described.

Figure 13:
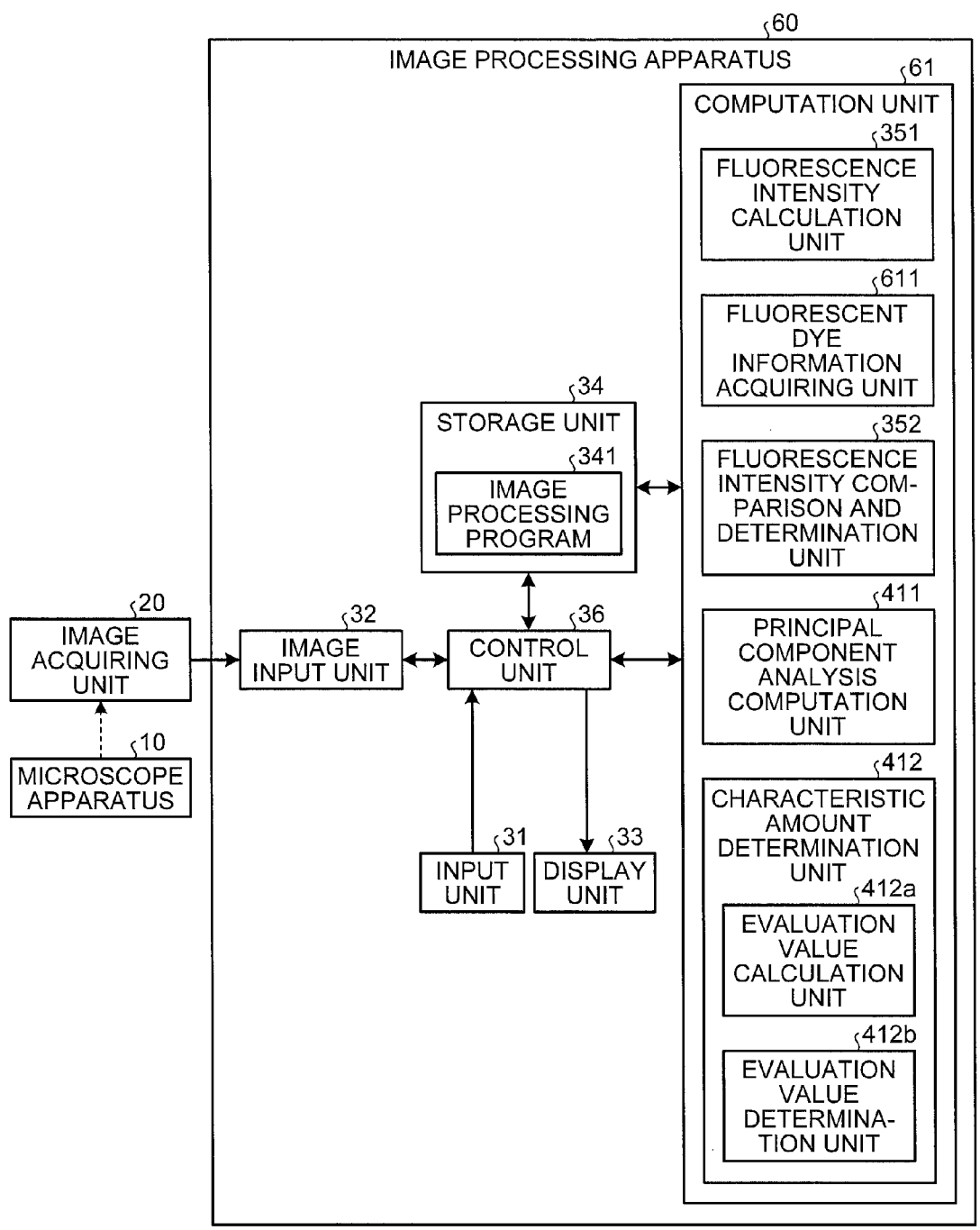
FIG. 13 is a block diagram illustrating a configuration of a microscope system according to a fifth embodiment of the present invention.

FIG. 13 is a block diagram illustrating a configuration of a microscope system according to a fifth embodiment. As illustrated in FIG. 13, a microscope system 5 according to the fifth embodiment includes, instead of the image processing apparatus 50 illustrated in FIG. 11, an image processing apparatus 60 having a computation unit 61.

The computation unit 61 further has, in addition to the configuration of the computation unit 51 illustrated in FIG. 11, a fluorescent dye information acquiring unit 611. The fluorescent dye information acquiring unit 611 acquires, according to a signal of which an input has been received by the input unit 31, information related to specified fluorescence from information related to known fluorescence (for example, fluorescence emitted by a commercially available fluorescent dye) held by the storage unit.

A configuration of the image processing apparatus 60 and a configuration of the whole microscope system 5, other than the fluorescent dye information acquiring unit 611, are similar to those described in the fourth embodiment.

Next, the operations of the microscope system 5 are described. The microscope system 5 is characterized in that determination is made on usability or non-usability of a fluorescent dye that a user is considering of using as a fluorescent dye to stain a fluorescence labeled antibody to be superimposed on a non-fluorescence stained specimen. The fluorescent dye that the user is considering of using is specified by a selection signal input by the user using the input unit 31.

Figure 14:
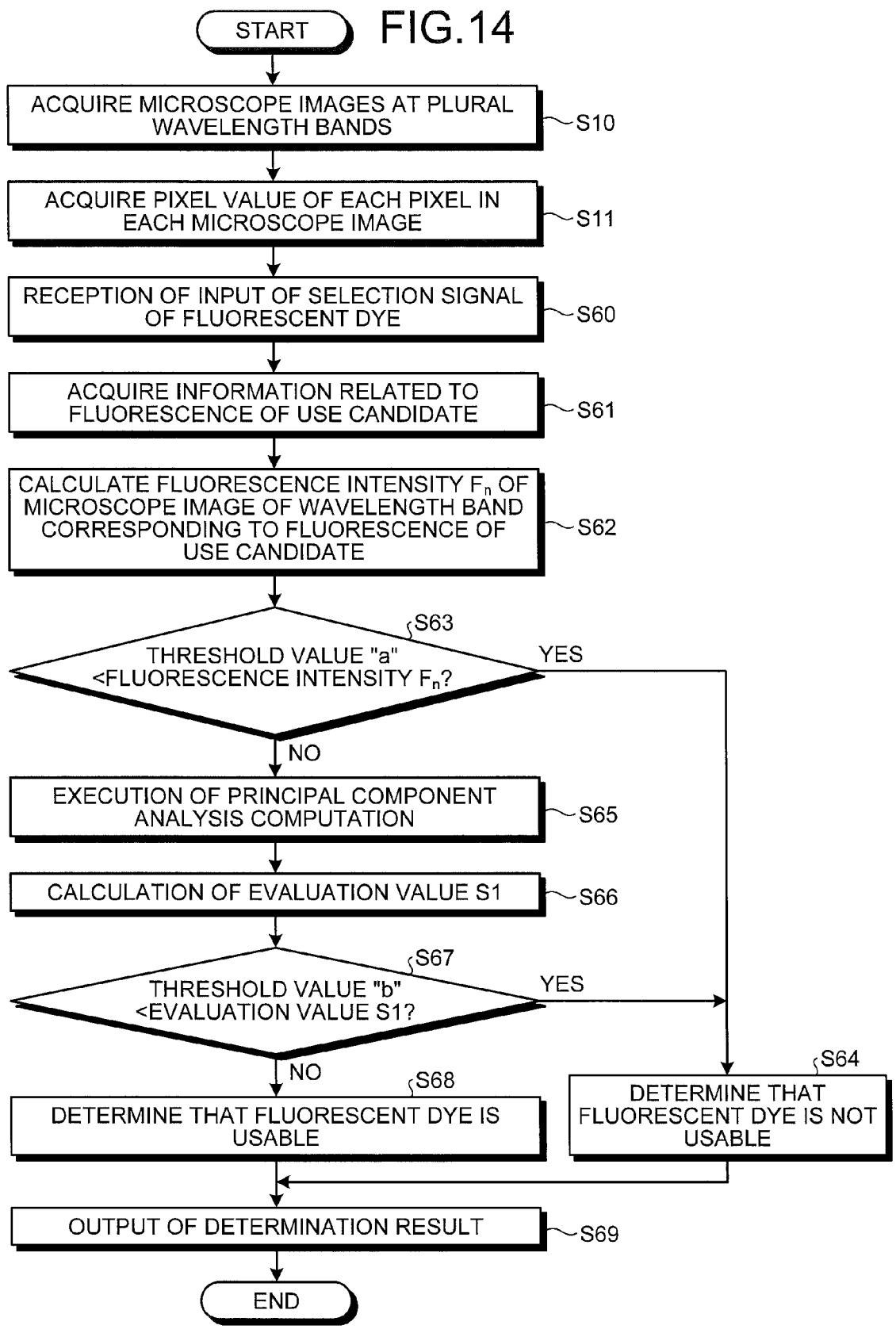
FIG. 14 is a flow chart illustrating operations of the microscope system illustrated in FIG. 13.

FIG. 14 is a flow chart illustrating the operations of the microscope system 5. Operations of steps S10 and S11 illustrated in FIG. 14 are common with the first embodiment.

When the input unit 31 receives the input of the selection signal of the fluorescent dye at step S60 following step S11, the fluorescent dye information acquiring unit 611 acquires the information (the wavelength band and the fluorescence intensity at each wavelength) related to fluorescence (hereinafter, referred to as "use candidate fluorescence") emitted by the fluorescent dye from the information related to the fluorescence held by the storage unit 34 (step S61).

At step S62, the fluorescence intensity comparison and determination unit 352 calculates a fluorescence intensity $F_n$ for a microscope image $G(\lambda_n)$ imaged at a wavelength band in which the use candidate fluorescence is distributed. A method of calculating the fluorescence intensity $F_n$ is similar to that described in the first embodiment.

At step S63, the fluorescence intensity comparison and determination unit 352 compares each fluorescence intensity $F_n$ calculated in step S62 with a specified threshold value "a" that has been set beforehand.

If there is at least one fluorescence intensity $F_n$ greater than the threshold value "a" (step S63: Yes), the fluorescence intensity comparison and determination unit 352 determines that the selected fluorescent dye is not usable (step S64).

On the contrary, if there is no fluorescence intensity $F_n$ greater than the threshold value "a" (step S63: No), the principal component analysis computation unit 411 executes principal component analysis computation with respect to quantities $x_{(n, k)}$ based on pixel values $P_k$ in a series of microscope images $G(\lambda_n)$ to calculate an eigenvector "u" that is a characteristic vector of auto-fluorescence (step S65). Details of a method of calculating the eigenvector "u" are similar to those described in the second embodiment.

At step S66, the evaluation value calculation unit 412a generates a characteristic vector "v" of the fluorescence from the information related to the use candidate fluorescence, and calculates, by using this characteristic vector "v" and the eigenvector "u" calculated in step S65, an evaluation value S1 given by Equation (4). If a plurality of eigenvectors "u" are calculated in step S65, a plurality of evaluation values S1 are calculated using each eigenvector "u".

At step S67, the evaluation value determination unit 412b compares the evaluation value S1 with a specified threshold value "b" that is set beforehand. If a plurality of evaluation values S1 are calculated in step S66, determination with respect to each evaluation value S1 is performed.

If there is at least one evaluation value S1 having a value greater than the threshold value "b" (step S67: Yes), the evaluation value determination unit 412b determines that the selected fluorescent dye is not usable (step S64). On the contrary, if there is no evaluation value S1 having a value greater than the threshold value "b" (step S67: No), it is determined that the selected fluorescent dye is usable (step S68).

At step S69, the computation unit 61 outputs a result of the determination in step S64 or S68. Accordingly, the control unit 36 causes the display unit 33 to display the result of the determination.

As described above, according to the fifth embodiment, a user is able to easily determine a fluorescent dye to stain a fluorescence labeled antibody to be superimposed on a non-fluorescence stained specimen by referring to the result of the determination displayed on the display unit 33. Therefore, the user is able to obtain an accurate observation result having small influence by auto-fluorescence, by performing fluorescence observation on a specimen multiply stained using such a fluorescent dye.

If the information related to the fluorescent dye that the user is considering of using is not stored in the storage unit 34, the information related to that fluorescent dye may be generated in the image processing apparatus 60. Specifically, by imaging a specimen stained only by that fluorescent dye at a plurality of wavelength bands using the microscope apparatus 10 and the image acquiring unit 20, a series of microscope images $G(\lambda_n)$ for respective wavelength bands are acquired. Subsequently, by acquiring quantities $x_{(n, k)}$ based on pixel values of respective pixels $P_k$ in the series of microscope images $G(\lambda_n)$ and performing principal component analysis computation with respect to these quantities $x_{(n, k)}$ based on these pixel values, an eigenvector is calculated. This eigenvector is a characteristic vector of fluorescence emitted by that fluorescent dye.

First Modified Example

Next, a first modified example of the first to fifth embodiments will be described.

A confocal laser microscope is preferably used as the microscope apparatus 10. If that is the case, strict limitation on a wavelength of excitation light to irradiate a specimen SP becomes possible and accurate comprehension in the image processing apparatus 30 and the like of a wavelength at which auto-fluorescence occurs becomes possible. Further, in the confocal laser microscope, by imaging and reconstructing images in optical serial sections with respect to a specimen having a thickness, three dimensional information is able to be imaged, and thus with respect to the specimen having the thickness, a wavelength band at which auto-fluorescence occurs at each position in a thickness direction is able to be comprehended accurately in the image processing apparatus 30 and the like.

Second Modified Example

Next, a second modified example of the first to fifth embodiments will be described.

A two-photon laser microscope may be preferably used as the microscope apparatus 10. In the two-photon laser microscope, with respect to a thick specimen of, for example, 100 µm or greater like a brain slice, an observation image in a deep part is obtainable, and thus a wavelength band of auto-fluorescence emitted from a thick specimen is able to be comprehended accurately in the image processing apparatus 30 and the like.

Third Modified Example

Next, a third modified example of the first to fifth embodiments will be described.

As a configuration of the image acquiring unit that acquires the microscope image for each wavelength band, instead of using the multiband camera, a camera that is able to perform imaging over a wide band may be used in combination with a filter unit that separates light incident on the camera into respective wavelengths.

Figure 15:
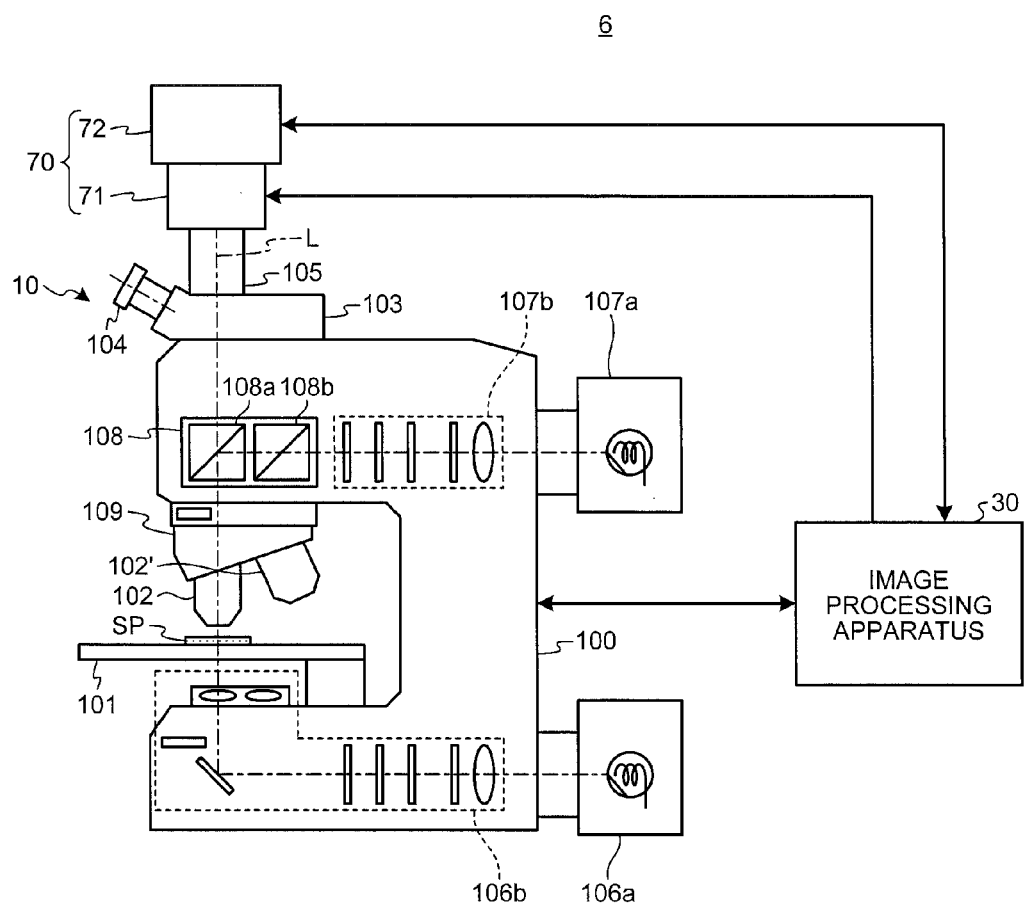
FIG. 15 is a schematic diagram illustrating an example of a configuration of a microscope apparatus according to a third modified example.

FIG. 15 is a schematic diagram illustrating an example of a configuration of a microscope system according to a third modified example. As illustrated in FIG. 15, a microscope system 6 according to the third modified example includes, instead of the image acquiring unit 20 illustrated in FIG. 2, an image acquiring unit 70, which has: a liquid crystal tunable filter 71 provided at an end portion of the imaging lens unit 105; and a camera 72 attached to the liquid crystal tunable filter 71. A configuration of the microscope system 2 other than the image acquiring unit 70 is similar to that illustrated in FIG. 2.

The liquid crystal tunable filter 71 operates under control of the image processing apparatus 30 and extracts an arbitrary wavelength component from light (observation light) incident via the imaging lens unit 105.

Figure 16:
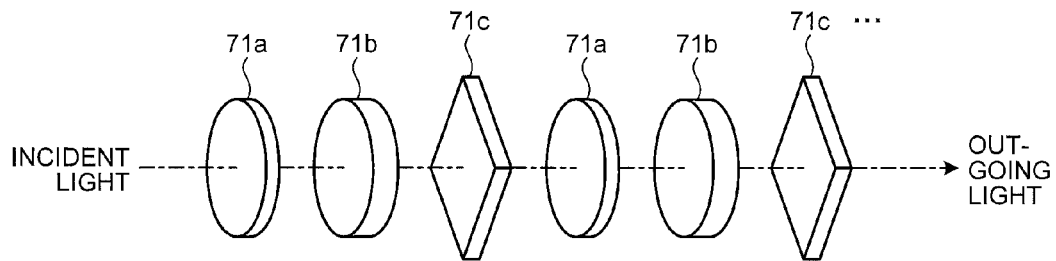
FIG. 16 is a diagram illustrating a configuration of a liquid crystal tunable filter.

As illustrated in FIG. 16, the liquid crystal tunable filter 71 has a structure repeatedly layered of plural stages each including a polarizer 71a, a birefringent filter 71b, and a liquid crystal (nematic liquid crystal) cell 71c, and is able to change a wavelength component extracted, in a unit of, for example, 1 nm, by changing a voltage to be applied on the liquid crystal cell 71c of each stage. A VariSpec liquid crystal tunable filter manufactured by Cambridge Research & Instrumentation, Inc. (CRi) (United States of America), for example, is known as such a liquid crystal tunable filter 71.

The camera 72 is imaging equipment that includes an imaging element such as a CCD, for example, and that is capable of imaging over a wide band including about 400 nm to about 900 nm, which is at least from a visible region to a near infrared region. The camera 72 operates under the control of the image processing apparatus 30, and causes the wavelength component extracted by the liquid crystal tunable filter 71 to be input and image data corresponding to this wavelength component to be output.

By imaging the specimen SP using the image acquiring unit 70 having such a configuration, a plurality of microscope images separated over a narrower band are obtainable. Accordingly, in the image processing apparatus 30, accurate determination of a wavelength band at which auto-fluorescence occurs is possible. Therefore, it becomes possible for a user to infallibly select, based on a result of determination in the image processing apparatus 30, a fluorescent dye having small influence of auto-fluorescence.

Fourth Modified Example

Next, as a fourth modified example of the first to fifth embodiments, another configuration of the image acquiring unit that acquires the microscope image of each wavelength band will be described.

Figure 17:
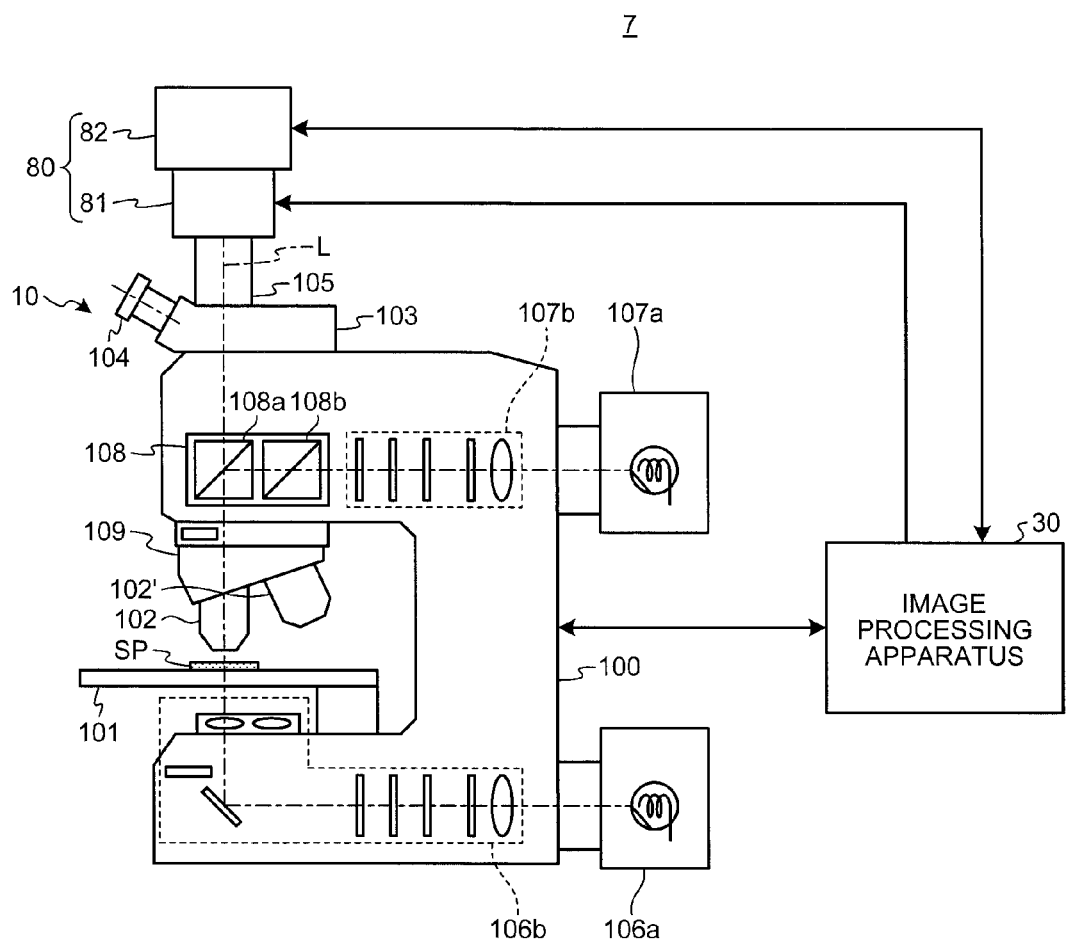
FIG. 17 is a schematic diagram illustrating an example of a configuration of a microscope apparatus according to a fourth modified example.

FIG. 17 is a schematic diagram illustrating an example of a configuration of a microscope system according to a fourth modified example. As illustrated in FIG. 17, a microscope system 7 according to the fourth modified example includes, instead of the image acquiring unit 20 illustrated in FIG. 2, an image acquiring unit 80, which has: an acousto-optic tunable wavelength filter 81 provided at an end portion of the imaging lens unit 105; and a camera 82 attached to the acousto-optic tunable wavelength filter 81. A configuration of the microscope system 3 other than the image acquiring unit 80 is similar to that illustrated in FIG. 2.

The acousto-optic tunable wavelength filter 81 operates under the control of the image processing apparatus 30 and extracts an arbitrary wavelength component from light (observation light) incident via the imaging lens unit 105.

Figure 18:
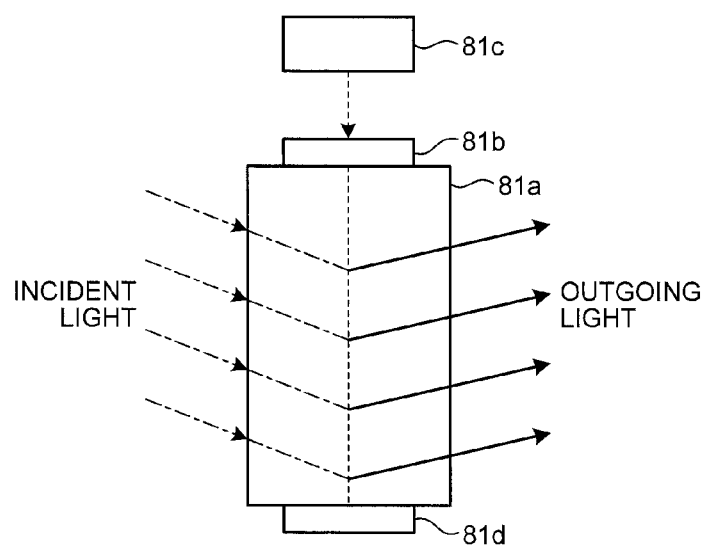
FIG. 18 is a diagram illustrating a principle of wavelength division in an acousto-optic tunable wavelength filter.

As illustrated in FIG. 18, the acousto-optic tunable wavelength filter 81 includes: an acousto-optic modulator 81a that is formed of a crystal having a high anisotropy like, for example, tellurium dioxide crystal, and that extracts and emits a wavelength component according to a frequency and an amplitude of a sound wave (ultrasonic wave) applied from incident light; a transducer (piezoelectric element) 81b that applies a sound wave to the acousto-optic modulator 81a by expanding and contracting according to an applied voltage; a high frequency oscillator 81c that applies the voltage to the transducer 81b; and a damper 81d that absorbs vibration of the acousto-optic modulator 81a. In such an acousto-optic tunable wavelength filter 81, by adjusting an oscillation frequency and an amplitude in the high frequency oscillator 81c and controlling the ultrasonic wave applied by the transducer 81b to the acousto-optic modulator 81a, the wavelength component extracted by the acousto-optic modulator 81a is able to be controlled.

The camera 82 is imaging equipment that includes, for example, an imaging element such as a CCD, and that is capable of imaging over a wide band including about 400 nm to about 900 nm, which is at least from a visible region to a near infrared region. The camera 82 operates under the control of the image processing apparatus 30, and causes the wavelength component extracted by the acousto-optic tunable wavelength filter 81 to be input and image data corresponding to this wavelength component to be output.

By imaging the specimen SP using the image acquiring unit 80 having such a configuration, a plurality of microscope images separated over a narrower band are obtainable. Further, the acousto-optic tunable wavelength filter 81 is not easily influenced by a temperature change, and thus even under an environment where, for example, temperature is high or temperature severely changes, a microscope image accurately reflecting auto-fluorescence emitted from a non-fluorescence stained specimen is obtainable. Therefore, even under such an environment, in the image processing apparatus 30, a wavelength band in which auto-fluorescence occurs is able to be accurately determined. Therefore, it becomes possible for a user to infallibly select, based on a result of determination in the image processing apparatus 30, a fluorescent dye having small influence of auto-fluorescence.

The above described first to fifth embodiments and the first to fourth modified examples are applicable to a case in which more than one type of fluorescence labeled antibody is superimposed on more than one type of non-fluorescent stain.

According to some embodiments, based on a plurality of microscope images acquired by imaging, at wavelength bands different from one another, a specimen subjected to non-fluorescent staining, characteristic amount representing auto-fluorescence emitted by the specimen are calculated, and thus a wavelength band of the auto-fluorescence emitted by a non-fluorescent dye is able to be determined readily.

It is to be understood that the present invention is not limited to the first to fifth embodiments and the first to fourth modified examples described above, but encompasses reasonable combinations of elements set forth in the first to fifth embodiments and the first to fourth modified examples. For example, some of the whole elements set forth in one of the embodiments may be omitted, or elements set forth in different embodiments may be combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   an interface configured to receive an input of a plurality of images acquired by imaging a specimen stained with non-fluorescent dye at a plurality of wavelength bands that are different from one another; and
   a processor comprising hardware, wherein the processor is configured to:
      calculate a characteristic amount representing auto-fluorescence emitted by the specimen based on the plurality of images; and
      determine a wavelength band of fluorescence where a fluorescence labeled antibody is superimposable or not superimposable on the specimen stained with the non-fluorescent dye based on the characteristic amount.

2. The image processing apparatus according to claim 1, wherein the characteristic amount is a fluorescence intensity calculated from a pixel value of a pixel in each image for each of the plurality of images, and
   wherein the processor is configured to determine the wavelength band of fluorescence by comparing the fluorescence intensity with a specified threshold value.

3. The image processing apparatus according to claim 1, wherein the processor is configured to:
   extract an intensity spectrum defined according to a wavelength based on the pixel value of the pixel in the plurality of images, and
   determine the wavelength band of fluorescence based on a correlation between the intensity spectrum and an intensity spectrum of known fluorescence.

4. The image processing apparatus according to claim 3, wherein the processor is configured to:
   calculate an eigenvector by principal component analysis computation with respect to a quantity based on the pixel value of the pixel in the plurality of images;
   calculate an evaluation value representing a correlation between the eigenvector and a characteristic vector corresponding to the intensity spectrum of the known fluorescence; and
   compare the evaluation value with a specified threshold value.

5. The image processing apparatus according to claim 4, wherein the evaluation value is a value acquired by normalizing an inner product of the characteristic vector and the eigenvector, and
   wherein the processor is configured to determine that fluorescence of a wavelength band corresponding to the characteristic vector is not superimposable, if the evaluation value is greater than the specified threshold value.

6. The image processing apparatus according to claim 4, wherein the evaluation value is an inner product of difference vectors between the characteristic vector and a vector acquired by projecting the eigenvector in a direction of the characteristic vector, and
   wherein the processor is configured to determine that fluorescence of a wavelength band corresponding to the characteristic vector is not superimposable, if the evaluation value is less than the specified threshold value.

7. The image processing apparatus according to claim 2, wherein the processor is configured to:
   extract an intensity spectrum defined according to a wavelength based on the pixel value of the pixel in the plurality of images;
   determine a wavelength band of fluorescence that is superimposable or not superimposable based on a correlation between the intensity spectrum and an intensity spectrum of known fluorescence; and
   determine a wavelength band of fluorescence that is superimposable or not superimposable, with respect to the wavelength band of the fluorescence determined to be superimposable.

8. The image processing apparatus according to claim 3, further comprising:
   a storage configured to store information on the known fluorescence.

9. A microscope system, comprising:
   the image processing apparatus according to claim 1;
   a microscope apparatus configured to perform fluorescence observation with respect to the specimen; and
   an image sensor configured to acquire the plurality of images by performing imaging at the plurality of wavelength bands that are different from one another.

10. The microscope system according to claim 9, wherein the image sensor is configured to perform imaging in a wavelength region including a visible region and a near infrared region.

11. An image processing method comprising:
   receiving an input of a plurality of images acquired by imaging a specimen stained with non-fluorescent dye at a plurality of wavelength bands that are different from one another;
   calculating a characteristic amount representing auto-fluorescence emitted by the specimen based on the plurality of images; and
   determining a wavelength band of fluorescence where a fluorescence labeled antibody is superimposable or not superimposable on the specimen stained with the non-fluorescent dye based on the characteristic amount.

12. A non-transitory computer-readable recording medium with an executable program stored thereon, wherein the program instructs a processor to perform:
   receiving an input of a plurality of images acquired by imaging a specimen stained with non-fluorescent dye at a plurality of wavelength bands that are different from one another;
   calculating a characteristic amount representing auto-fluorescence emitted by the specimen based on the plurality of images; and
   determining a wavelength band of fluorescence where a fluorescence labeled antibody is superimposable or not superimposable on the specimen stained with the non-fluorescent dye based on the characteristic amount.

\* \* \* \* \*